(12) United States Patent
Fu (10) Patent No.: US 11,583,174 B2
(45) Date of Patent: Feb. 21, 2023

(54) ENDOSCOPE DEVICE WITH FLEXIBLE CIRCUIT BOARD TO CONNECT DISTAL END SENSOR TO HANDLE

(71) Applicant: ALTEK BIOTECHNOLOGY CORPORATION, Hsinchu (TW)

(72) Inventor: Chin-Jui Fu, Taichung (TW)

(73) Assignee: ALTEK BIOTECHNOLOGY CORPORATION, Hsinchu (TW)

( * ) Notice: Subject to any disclaimer, the term of this patent is extended or adjusted under 35 U.S.C. 154(b) by 323 days.

(21) Appl. No.: 17/005,329

(22) Filed: Aug. 28, 2020

(65) Prior Publication Data

US 2021/0345868 A1 Nov. 11, 2021

(30) Foreign Application Priority Data

May 11, 2020 (TW) ................................. 109205659

(51) Int. Cl.
*A61B 1/00* (2006.01)
*A61B 1/06* (2006.01)
*A61B 1/05* (2006.01)

(52) U.S. Cl.
CPC .......... *A61B 1/0676* (2013.01); *A61B 1/0014* (2013.01); *A61B 1/00066* (2013.01); *A61B 1/05* (2013.01); *A61B 2562/166* (2013.01)

(58) Field of Classification Search
CPC ..... A61B 1/00066; A61B 1/0014; A61B 1/05; A61B 2562/166; A61B 1/0676

USPC ......................................................... 600/131
See application file for complete search history.

(56) References Cited

U.S. PATENT DOCUMENTS

| | | | |
|---|---|---|---|
| 2015/0378144 A1* | 12/2015 | Handte | G02B 23/2484 |
| | | | 250/208.1 |
| 2017/0071462 A1* | 3/2017 | Wieters | A61B 1/043 |
| 2020/0138271 A1* | 5/2020 | Toth | A61B 1/0676 |

FOREIGN PATENT DOCUMENTS

| | | |
|---|---|---|
| CN | 106233183 | 12/2016 |
| CN | 104995907 | 5/2019 |
| CN | 209574634 | 11/2019 |
| TW | I454242 | 10/2014 |
| TW | I520709 | 2/2016 |

* cited by examiner

*Primary Examiner* — Timothy J Neal
*Assistant Examiner* — James Edward Boice
(74) *Attorney, Agent, or Firm* — JCIPRNET (57) ABSTRACT

The disclosures provides an endoscope device which includes a handle portion including a main circuit board, a clamping portion connected to the handle portion, and an insertion portion connected to the clamping portion and including a lens, an image sensor corresponding to the lens, and a flexible circuit board electrically connected to the image sensor, wherein the lens and the image sensor are located at a distal end of the insertion portion away from the clamping portion, and the flexible circuit board extends from the distal end through the clamping portion to the handle portion and is electrically connected to the main circuit board.

18 Claims, 8 Drawing Sheets

ENDOSCOPE DEVICE WITH FLEXIBLE CIRCUIT BOARD TO CONNECT DISTAL END SENSOR TO HANDLE

CROSS-REFERENCE TO RELATED APPLICATION

This application claims the priority benefit of Taiwan application serial no. 109205659, filed on May 11, 2020. The entirety of the above-mentioned patent application is hereby incorporated by reference herein and made a part of this specification.

BACKGROUND

Technical Field

This disclosure relates to an endoscope device and an insertion portion, in particular, to an endoscope device and an insertion portion for video purposes.

Description of Related Art

Due to the technological advancement of semiconductors and micromachines, video endoscopes have become widely used. Compared with a traditional optical endoscope that has a complex optical system, a video endoscope has a simple structure by which the endoscope is miniaturized in size while improved in resolution and image quality. Therefore, there has been a trend in system development in which an image sensor and a lighting device are moved to a distal end of the endoscope.

In a conventional endoscope, signal transmission between the distal end and a handle portion is achieved through a wire. However, due to the fact that the size of the endoscope in the radial direction is reduced and that the parts such as an electronic component, the image sensor, a light source for illumination and the like are concentrated at the distal end of the endoscope, stacking density of the components located at the distal end of the endoscope is increased and the number of wires required is greatly increased. As a result, the endoscope may not have sufficient internal space to accommodate so many wires. Moreover, the wires need to be welded one by one during assembly, which is quite inconvenient.

SUMMARY

The disclosure provides an endoscope device and an insertion portion, in which, instead of using a plurality of wires as in a conventional design, a flexible circuit board is provided extending from a distal end to a handle portion through a clamping portion.

An endoscope device of the disclosure includes a handle portion, a clamping portion, and an insertion portion. The handle portion includes a main circuit board. The clamping portion is connected to the handle portion. The insertion portion is connected to the clamping portion and includes a lens, an image sensor corresponding to the lens, and a flexible circuit board electrically connected to the image sensor, wherein the lens and the image sensor are located at a distal end of the insertion portion away from the clamping portion, and the flexible circuit board extends from the distal end to the handle portion through the clamping portion and is electrically connected to the main circuit board.

An insertion portion of the disclosure is suitable for an endoscope device and is connected to a handle portion through a clamping portion. The insertion portion includes a lens, an image sensor corresponding to the lens, and a flexible circuit board electrically connected to the image sensor, wherein the lens and the image sensor are located at a distal end of the insertion portion away from the clamping portion. The flexible circuit board passes through the insertion portion from the distal end, is adapted to extend through the clamping portion to the handle portion and is electrically connected to a main circuit board in the handle portion.

In an embodiment of the disclosure, the insertion portion further includes a light source electrically connected to the flexible circuit board. The light source is disposed at the distal end and is located beside the lens.

In an embodiment of the disclosure, the flexible circuit board includes a first segment extending from the distal end to the handle portion and a plurality of segments located at the distal end and connected to each other in a bent manner. The insertion portion further includes a lens holder located at the distal end. The lens is disposed in the lens holder. The plurality of segments partially surround the lens holder.

In an embodiment of the disclosure, the plurality of segments include a second segment connected to the first segment in a bent manner, a third segment and a fourth segment connected to two sides of the second segment in a bent manner, a fifth segment connected to the fourth segment in a bent manner, and a sixth segment connected to the third segment in a bent manner. The second segment, the third segment, and the sixth segment partially surround the lens holder.

In an embodiment of the disclosure, the insertion portion further includes a circuit board holder. The circuit board holder is disposed beside the lens holder. The circuit board holder and the lens holder jointly clamp the fifth segment. The image sensor is disposed at the fifth segment.

In an embodiment of the disclosure, one of the circuit board holder and the lens holder includes a fixed convex portion, and the other includes a fixed recess portion. The fixed convex portion extends into the fixed recess portion. An extension direction of the fixed convex portion is parallel to an extension direction of the insertion portion.

In an embodiment of the disclosure, the endoscope device further includes a heat dissipation column extending from the insertion portion to the clamping portion. The flexible circuit board includes a first segment extending from the distal end to the handle portion and a seventh segment located at least in the clamping portion and extending from the first segment, and the first segment and the seventh segment cover the heat dissipation column.

In an embodiment of the disclosure, the seventh segment extends from the clamping portion to the handle portion and is connected to the main circuit board.

In an embodiment of the disclosure, a thickness of the flexible circuit board is between 0.15 mm and 0.18 mm.

In an embodiment of the disclosure, the flexible circuit board includes a first segment extending from the distal end to the handle portion, and a width of the first segment does not exceed 3 mm.

In an embodiment of the disclosure, the flexible circuit board includes a first segment extending from the distal end to exceed the insertion portion, and a width of the first segment does not exceed 3 mm.

Based on the above, in the endoscope device of the disclosure, the lens and the image sensor are located at the distal end of the insertion portion away from the clamping portion. The flexible circuit board electrically connected to the image sensor extends from the distal end to the handle portion through the clamping portion and is electrically connected to the main circuit board of the handle portion. A conventional endoscope device uses a plurality of wires to electrically connect the distal end with the handle portion, and is not easy to assemble since a large number of wires need to be disposed in limited space and need to be welded one by one. In contrast, in the endoscope device of the disclosure, a circuit may be disposed on the flexible circuit board, which may greatly reduce the volume of the endoscope device and provide convenience in assembly and disposition.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF THE EMBODIMENTS

Figure 1:
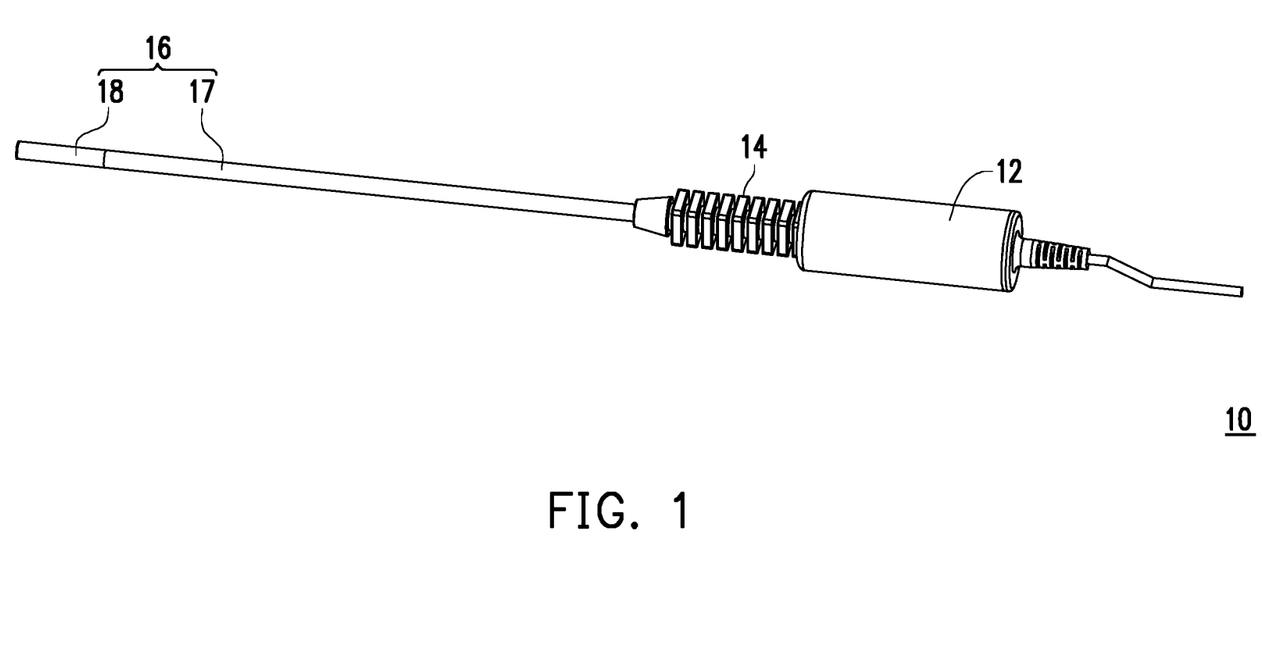
FIG. 1 is a schematic diagram of an endoscope device according to an embodiment of the disclosure.

FIG. 1 is a schematic diagram of an endoscope device according to an embodiment of the disclosure. Referring to FIG. 1, an endoscope device 10 of this embodiment can be applied to a video endoscope, but the disclosure is not limited thereto. The endoscope device 10 includes a handle portion 12, a clamping portion 14, and an insertion portion 16. The handle portion 12 is for an operator to hold. The clamping portion 14 is connected to the handle portion 12, and the insertion portion 16 is connected to the clamping portion 14. The insertion portion 16 includes an extension portion 17 connected to the clamping portion 14 and a distal end 18 away from the clamping portion 14.

The insertion portion 16 may be integrally formed with the handle portion 12 and the clamping portion 14. Alternatively, the insertion portion 16 may be disposable and can be replaced with a new insertion portion 16 after use.

Figure 2:
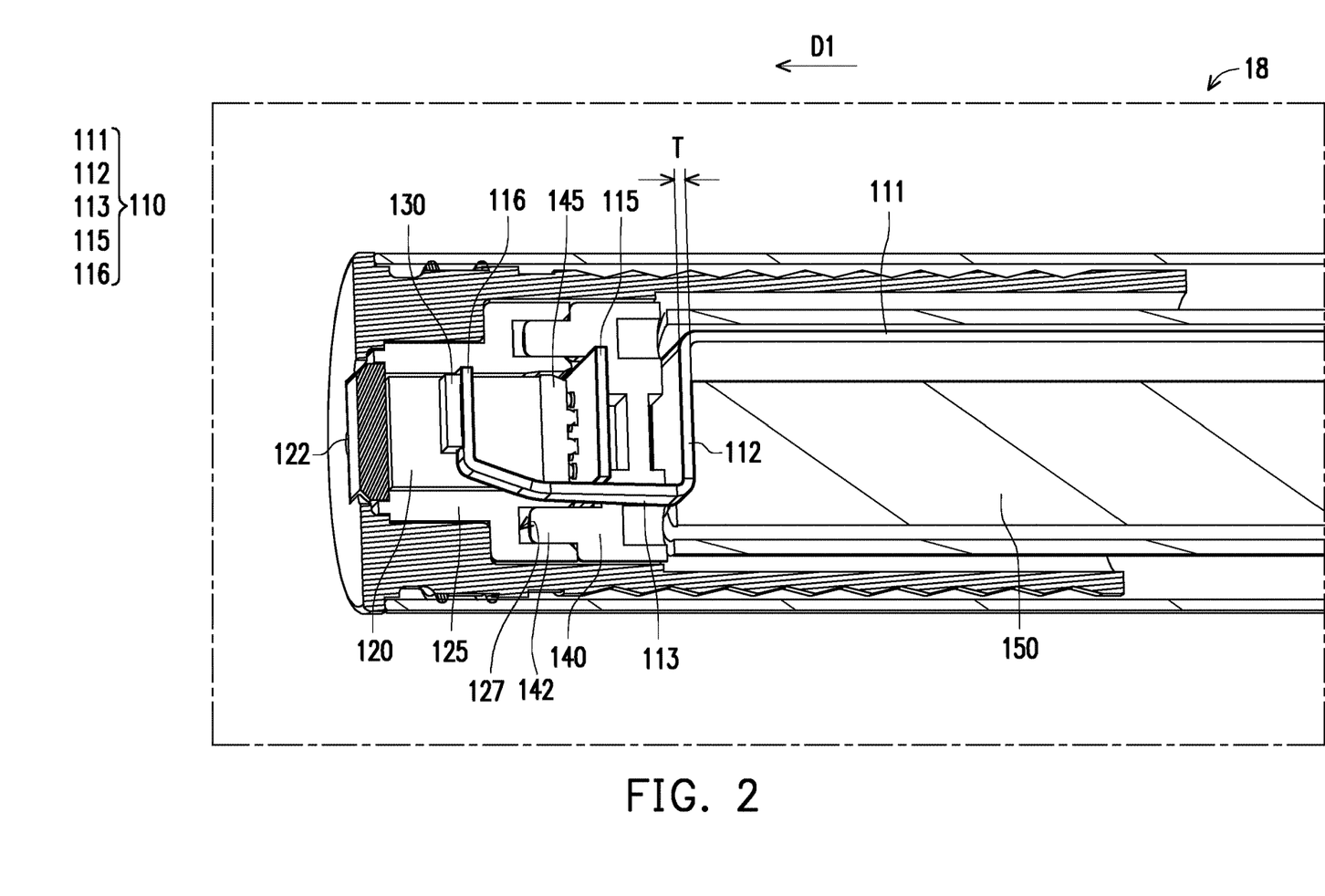
FIG. 2 is a schematic cross-sectional diagram of a distal end of the endoscope device of FIG. 1.
Figure 3:
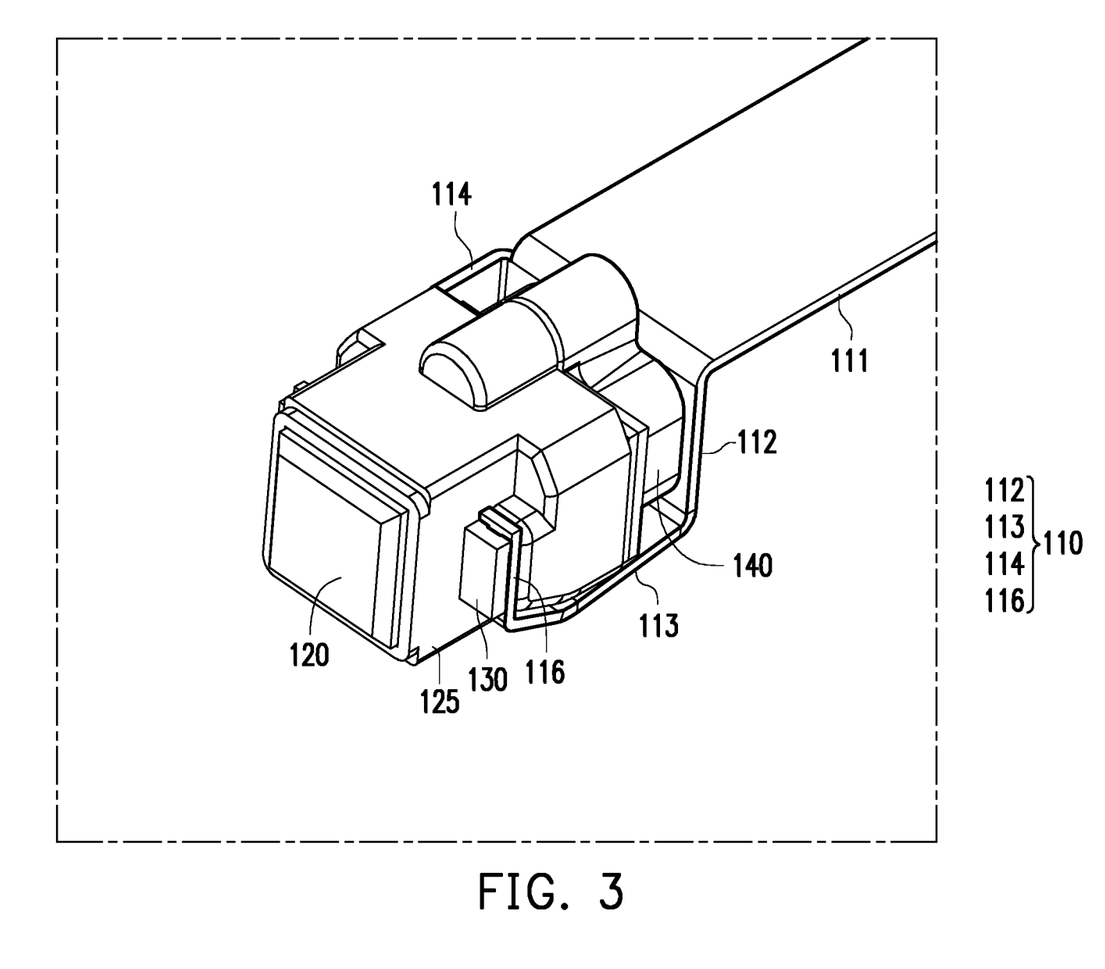
FIG. 3 is a schematic perspective diagram of the distal end of the endoscope device of FIG. 1, wherein a housing of the distal end is omitted.
Figure 4:
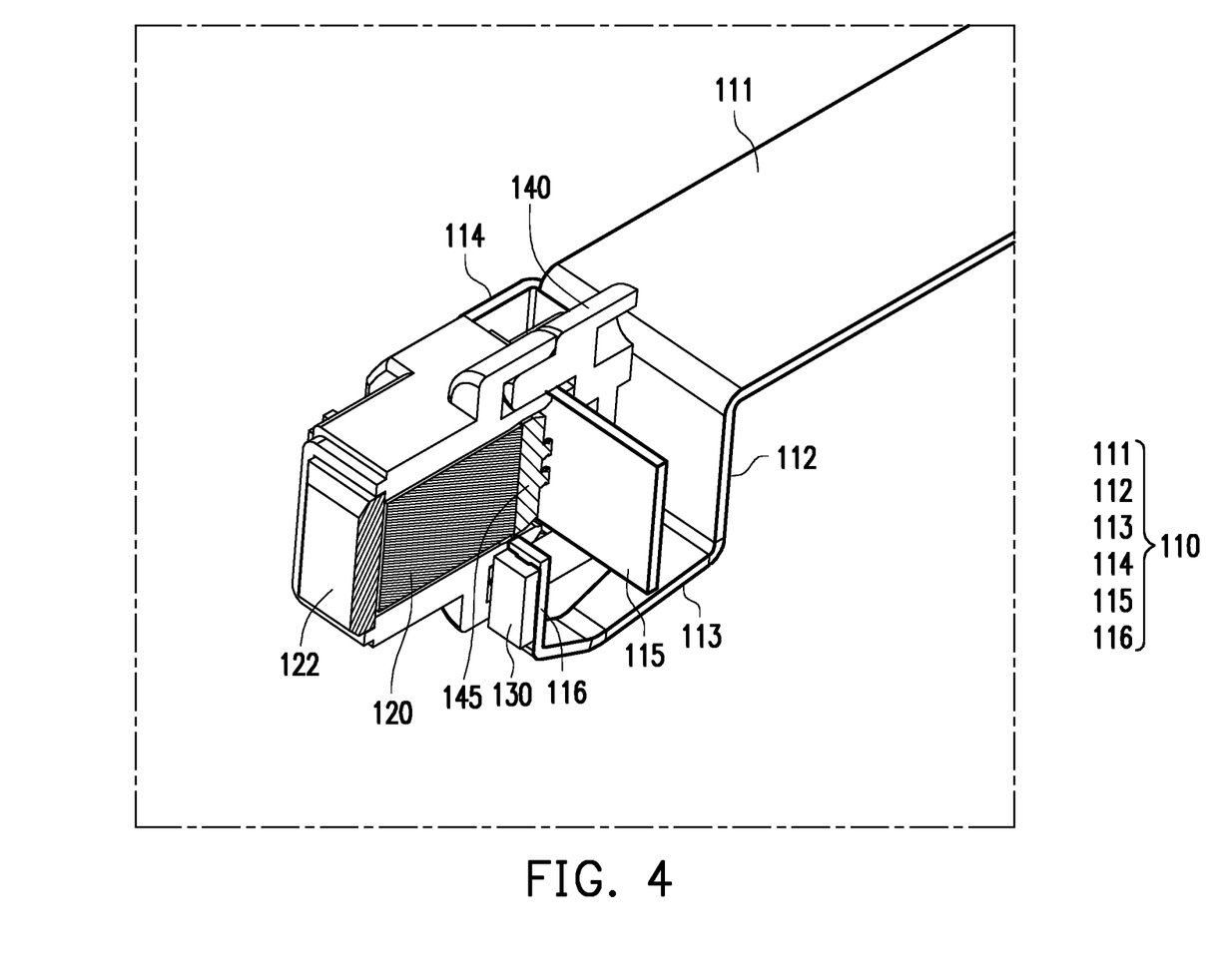
FIG. 4 is a schematic cutaway diagram of a lens and an image sensor of FIG. 3.
Figure 5:
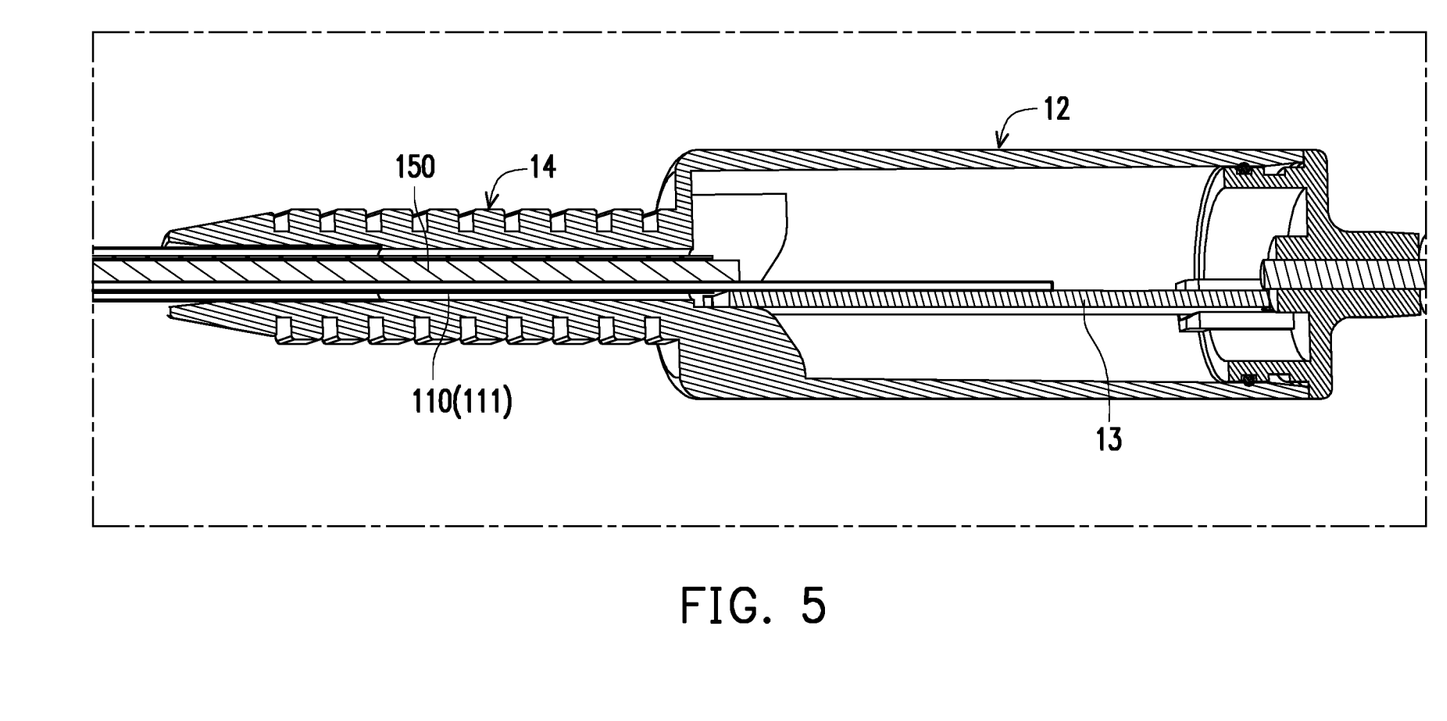
FIG. 5 is a schematic cross-sectional diagram of a handle portion and a part of a clamping portion of the endoscope device of FIG. 1.

FIG. 2 is a schematic cross-sectional diagram of the distal end of the endoscope device of FIG. 1. FIG. 3 is a schematic perspective diagram of the distal end of the endoscope device of FIG. 1, wherein a housing of the distal end is omitted. FIG. 4 is a schematic cutaway diagram of a lens and an image sensor of FIG. 3. FIG. 5 is a schematic cross-sectional diagram of the handle portion and a part of the clamping portion of the endoscope device of FIG. 1.

Referring to FIGS. 2 to 5, the insertion portion 16 (marked in FIG. 1) includes a lens 120, an image sensor 145 corresponding to the lens 120, and a flexible circuit board 110 electrically connected to the image sensor 145, wherein the lens 120 and the image sensor 145 are located at the distal end 18 of the insertion portion 16 away from the clamping portion 14. An optical lens 122 is located on a front side of the lens 120. In this embodiment, the insertion portion 16 further includes a light source 130 electrically connected to the flexible circuit board 110, and the light source 130 is disposed at the distal end 18 and is located beside the lens 120.

In a conventional endoscope, signal transmission between a distal end and a handle portion is achieved through a wire. However, due to the fact that the size of the endoscope in the radial direction is reduced and that the parts such as an electronic component, the image sensor, a light source for illumination and the like are concentrated at the distal end of the endoscope, stacking density of the components located at the distal end of the endoscope is increased and the number of wires required is greatly increased. As a result, the endoscope may not have sufficient internal space to accommodate so many wires. Moreover, the wires need to be welded one by one during assembly, which is quite inconvenient.

A conventional endoscope device uses a plurality of (for example, eight to twelve) wires to electrically connect the distal end with the handle portion, and it is difficult to dispose so many wires in limited space. In contrast, in the endoscope device 10 of this embodiment, a circuit of an electronic component such as the image sensor 145 and the light source 130 may be disposed on the flexible circuit board 110. The flexible circuit board 110 extends from the distal end 18 to the handle portion 12 through the clamping portion 14 and is electrically connected to the main circuit board 13 (marked in FIG. 5) of the handle portion 12.

Since the endoscope device 10 has a quite small caliber, the width of the flexible circuit board 10 is limited. In this embodiment, the flexible circuit board 110 may be a single-sided circuit board or a double-sided circuit board, depending on circuit requirements. A circuit may be designed to have a fine pitch so that the signal transmission between the distal end 18 and the handle portion 12 is possible while the flexible circuit board 110 maintains a narrow shape. Compared with the conventional design including a plurality of wires, in this embodiment, the volume of the transmission structure is greatly reduced, and assembly and disposition are easy.

It is worth mentioning that the flexible circuit board 110 may supply power and transmit an image signal. Since the image signal needs to be transmitted from the distal end 18 to the handle portion 12, impedance is required to control a transmission path of the image signal so that the occurrence of a defective image caused by attenuation of the image signal can be avoided. In this embodiment, a thickness T of the flexible circuit board 110 is between 0.15 mm and 0.18 mm.

By calculation, it is known that, when the thickness T of the flexible circuit board 110 is greater than 0.15 mm, 100 ohm impedance matching can be achieved. Compared with a conventional wire which may only provide 50 ohm impedance matching, in this embodiment, the impedance matching effect is improved using the flexible circuit board 110. In addition, when the thickness T of the flexible circuit board 110 is less than 0.18 mm, the internal arrangement of the endoscope device 10 can be avoided being affected by an excessive thickness.

As shown in FIGS. 2 and 3, the flexible circuit board 110 includes a first segment 111 extending from the distal end 18 to the handle portion 12 and a plurality of segments located at the distal end 18 and connected to each other in a bent manner. The insertion portion 16 further includes a lens holder 125 at the distal end 18. The lens 120 is disposed in the lens holder 125. A material of the lens holder 125 includes plastic, thermally conductive plastic, or metal, and may facilitate heat dissipation. However, the material of the lens holder 125 is not limited to those mentioned above.

The segments located at the distal end 18 of the flexible circuit board 110 partially surround the lens holder 125. In detail, the segments located at the distal end 18 include a second segment 112 connected to the first segment 111 in a bent manner, a third segment 113 and a fourth segment 114 connected to two sides of the second segment 112 in a bent manner, a fifth segment 115 connected to the fourth segment 114 in a bent manner, and a sixth segment 116 connected to the third segment 113 in a bent manner. The second segment 112, the third segment 113, and the sixth segment 116 partially surround the lens holder 125. The sixth segment 116 rests on the lens holder 125 and is located beside the lens 120, and the light source 130 is disposed at the sixth segment 116.

In this embodiment, to ensure an alignment between the image sensor 145 and the lens 120, the distal end 18 of the insertion portion 16 further includes a circuit board holder 140. The circuit board holder 140 is disposed beside the lens holder 125, and the circuit board holder 140 and the lens holder 125 jointly clamp the fifth segment 115. The image sensor 145 is disposed at the fifth segment 115. A material of the circuit board holder 140 includes plastic or thermally conductive plastic, and may facilitate heat dissipation. However, the material of the circuit board holder 140 is not limited to those mentioned above.

In addition, one of the circuit board holder 140 and the lens holder 125 includes a fixed convex portion 142 and the other includes a fixed recess portion 127, and the fixed convex portion 142 extends into the fixed recess portion 127. Therefore, the circuit board holder 140 and the lens holder 125 can be well positioned with respect to each other. In this embodiment, the fixed convex portion 142 and the insertion portion 16 both extend along an extension direction D1.

Figure 6:
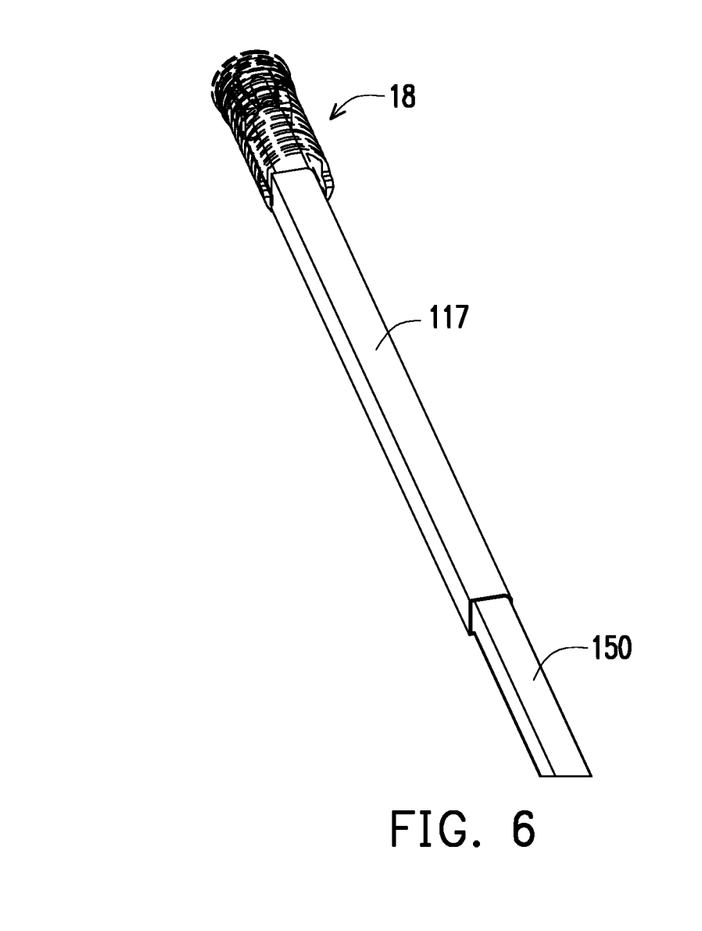
FIG. 6 is a schematic diagram of the inside of an insertion portion and the clamping portion of the endoscope device of FIG. 1.
Figure 7:
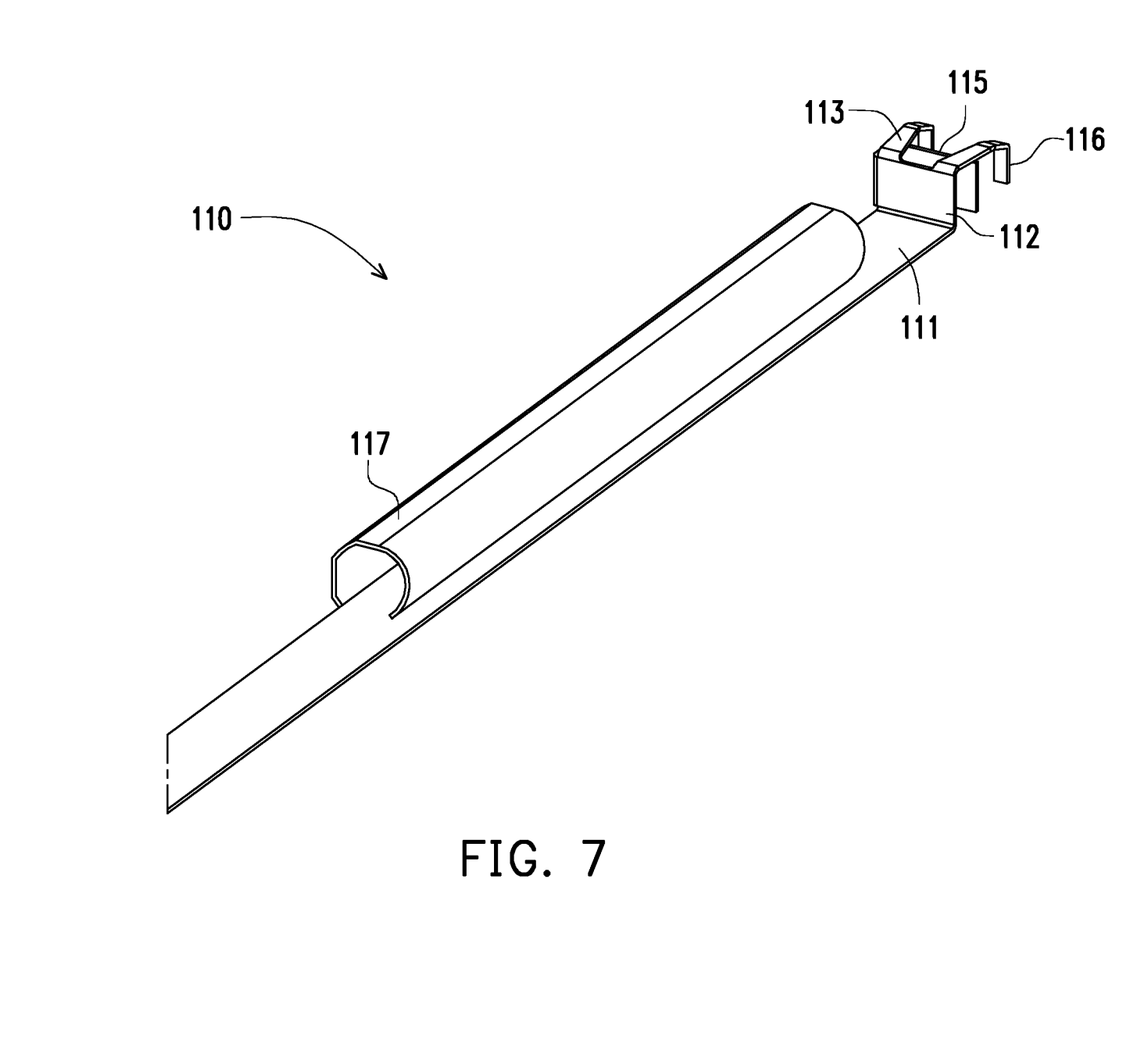
FIG. 7 is a schematic partial diagram of a flexible circuit board of the endoscope device of FIG. 1.

FIG. 6 is a schematic diagram of the inside of the insertion portion and the clamping portion of the endoscope device of FIG. 1. Referring to FIG. 6, the endoscope device 10 further includes a heat dissipation column 150 extending from the insertion portion 16 to the clamping portion 14. FIG. 7 is a schematic partial diagram of the flexible circuit board of the endoscope device of FIG. 1. Referring to FIG. 7, the flexible circuit board 110 includes the first segment 111 extending from the distal end 18 to the handle portion 12, and a seventh segment 117 located at least in the clamping portion 14 and extending from the first segment 111.

As shown in FIG. 6, the first segment 111 and the seventh segment 117 cover the heat dissipation column 150. The circuits on the first segment 111 and the seventh segment 117 may be designed to avoid contact with the heat dissipation column 150. The design that the first segment 111 and the seventh segment 117 cover the heat dissipation column 150 enables the heat of the flexible circuit board 110 to be transferred to the heat dissipation column 150 by conduction or radiation, and heat dissipation is accelerated.

In addition, in FIG. 7, the seventh segment 117 of the flexible circuit board 110 is connected to the first segment 111 at an entire lateral side, and only the first segment 111 extends to the handle portion 12. In other words, power, a control signal, and the image signal of the flexible circuit board 110 are transmitted to the main circuit board 13 through the first segment 111.

Figure 8:
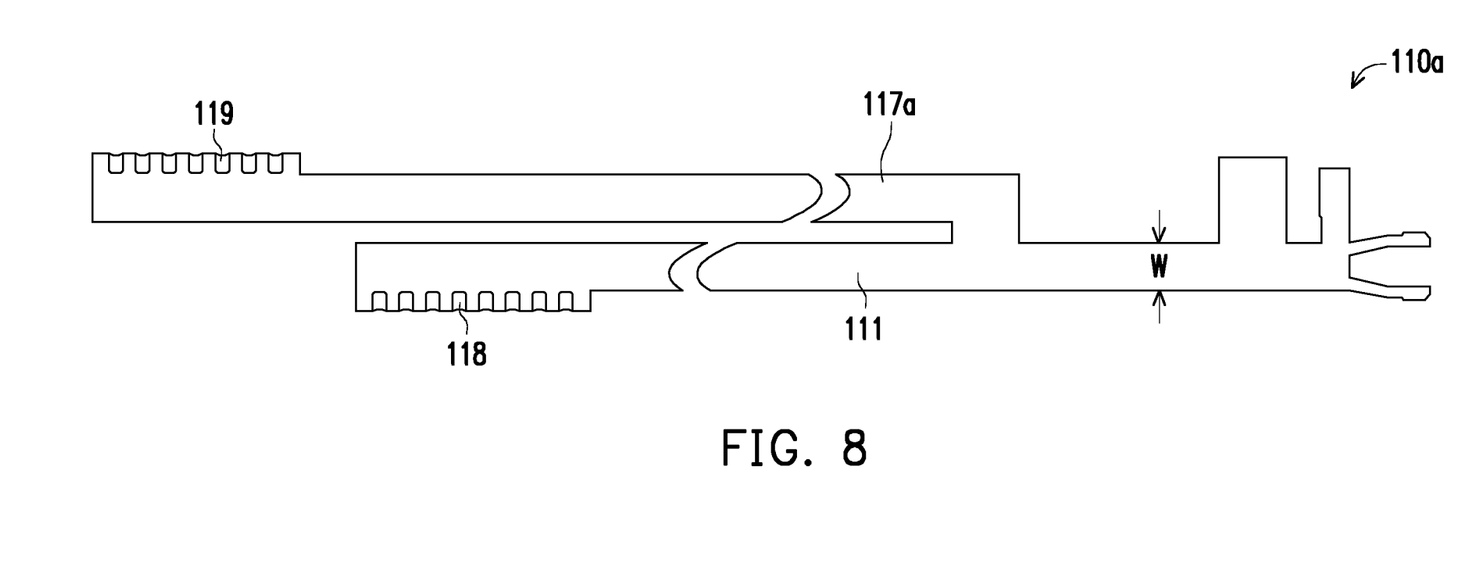
FIG. 8 is a schematic flattened diagram of a flexible circuit board of an endoscope device according to another embodiment of the disclosure.

FIG. 8 is a schematic flattened diagram of a flexible circuit board of an endoscope device according to another embodiment of the disclosure. Referring to FIG. 8, a main difference between a flexible circuit board 110a of FIG. 8 and the flexible circuit board 110 of FIG. 7 is that in this embodiment, a seventh segment 117a is only partially connected to the first segment 111, and the seventh segment 117a may extend from the clamping portion 14 to the handle portion 12 and be connected to the main circuit board 13. In detail, in this embodiment, the first segment 111 includes a pad 118 that may be connected to the main circuit board 13. In addition, the seventh segment 117a also includes a pad 119 that may be connected to the main circuit board 13.

In this embodiment, a width W of the first segment 111, for example, does not exceed 3 mm. However, the width W having such a value is only sufficient for disposing the circuits of a power supply and the control signal. Therefore, the seventh segment 117a is particularly designed for a circuit for transmitting the image signal to be disposed, such that the image signal can be transmitted from the distal end 18 to the main circuit board 13 of the handle portion 12 and a satisfactory impedance matching effect on the image signal can be provided. During assembly, a connected portion between the seventh segment 117a and the first segment 111 may be bent in advance of the assembly process.

In summary, in the endoscope device of the disclosure, the lens and the image sensor are located at the distal end of the insertion portion away from the clamping portion. The flexible circuit board electrically connected to the image sensor extends from the distal end to the handle portion through the clamping portion and is electrically connected to the main circuit board of the handle portion. A conventional endoscope device uses a plurality of wires to electrically connect the distal end with the handle portion, and is not easy to assemble since a large number of wires need to be disposed in limited space and need to be welded one by one. In contrast, in the endoscope device of the disclosure, a circuit may be disposed on the flexible circuit board, which may greatly reduce the volume of the endoscope device and provide convenience in assembly and disposition.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. An endoscope device, comprising:
   a handle portion comprising a main circuit board;
   a clamping portion connected to the handle portion; and
   an insertion portion connected to the clamping portion and comprising a lens, an image sensor corresponding to the lens, and a flexible circuit board electrically connected to the image sensor, wherein the lens and the image sensor are located at a distal end of the insertion portion away from the clamping portion, and the flexible circuit board extends from the distal end through the clamping portion to the handle portion and is electrically connected to the main circuit board,
   wherein the flexible circuit board comprises a first segment extending from the distal end to the handle portion, a second segment connected to the first segment in a bent manner, a third segment and a fourth segment connected to two sides of the second segment in a bent manner, a fifth segment connected to the fourth segment in a bent manner, and a sixth segment connected to the third segment in a bent manner, wherein the fifth segment is located between the sixth segment and the second segment.

2. The endoscope device according to claim 1, wherein the insertion portion further comprises a light source electrically connected to the flexible circuit board, and the light source is disposed at the distal end and located beside the lens.

3. The endoscope device according to claim 1, wherein the insertion portion further comprises a lens holder at the distal end, the lens is disposed in the lens holder, and the plurality of segments partially surround the lens holder.

4. The endoscope device according to claim 3, wherein the second segment, the third segment, and the sixth segment partially surround the lens holder.

5. The endoscope device according to claim 4, wherein the insertion portion further comprises a circuit board holder, the circuit board holder is disposed beside the lens holder, the circuit board holder and the lens holder jointly clamp the fifth segment, and the image sensor is disposed at the fifth segment.

6. The endoscope device according to claim 5, wherein one of the circuit board holder and the lens holder comprises a fixed convex portion and the other comprises a fixed recess portion, the fixed convex portion extends into the fixed recess portion, and an extension direction of the fixed convex portion is parallel to an extension direction of the insertion portion.

7. The endoscope device according to claim 1, further comprising a heat dissipation column extending from the insertion portion to the clamping portion, wherein the flexible circuit board comprises a seventh segment located at least in the clamping portion and extending from the first segment, and the first segment and the seventh segment cover the heat dissipation column.

8. The endoscope device according to claim 7, wherein the seventh segment extends from the clamping portion to the handle portion and is connected to the main circuit board.

9. The endoscope device according to claim 1, wherein a thickness of the flexible circuit board is between 0.15 mm and 0.18 mm.

10. The endoscope device according to claim 1, wherein a width of the first segment does not exceed 3 mm.

11. An insertion portion for an endoscope device, connected to a handle portion through a clamping portion, the insertion portion comprising:

a lens;

an image sensor corresponding to the lens; and a flexible circuit board electrically connected to the image sensor, wherein the lens and the image sensor are located at a distal end of the insertion portion away from the clamping portion, and the flexible circuit board passes through the insertion portion from the distal end, is adapted to extend through the clamping portion to the handle portion and is electrically connected to a main circuit board in the handle portion, wherein the flexible circuit board comprises a first segment extending from the distal end to the handle portion, a second segment connected to the first segment in a bent manner, a third segment and a fourth segment connected to two sides of the second segment in a bent manner, a fifth segment connected to the fourth segment in a bent manner, and a sixth segment connected to the third segment in a bent manner, wherein the fifth segment is located between the sixth segment and the second segment.

12. The insertion portion according to claim 11, wherein the insertion portion further comprises a light source electrically connected to the flexible circuit board, and the light source is disposed at the distal end and located beside the lens.

13. The insertion portion according to claim 11, wherein the insertion portion further comprises a lens holder at the distal end, the lens is disposed in the lens holder, and the plurality of segments partially surround the lens holder.

14. The insertion portion according to claim 13, wherein the second segment, the third segment, and the sixth segment partially surround the lens holder.

15. The insertion portion according to claim 14, wherein the insertion portion further comprises a circuit board holder, the circuit board holder is disposed beside the lens holder, the circuit board holder and the lens holder jointly clamp the fifth segment, and the image sensor is disposed at the fifth segment.

16. The insertion portion according to claim 15, wherein one of the circuit board holder and the lens holder comprises a fixed convex portion and the other comprises a fixed recess portion, the fixed convex portion extends into the fixed recess portion, and an extension direction of the fixed convex portion is parallel to an extension direction of the insertion portion.

17. The insertion portion according to claim 11, wherein a thickness of the flexible circuit board is between 0.15 mm and 0.18 mm.

18. The insertion portion according to claim 11, wherein a width of the first segment does not exceed 3 mm.

\* \* \* \* \*